(12) United States Patent
Guazzi

(10) Patent No.: US 6,897,333 B2
(45) Date of Patent: May 24, 2005

(54) PROCESS FOR THE PREPARATION OF FIBRATES

(75) Inventor: Giuseppe Guazzi, Mulazzano (IT)

(73) Assignee: Solchem Italiana S.p.A., Mulazzano (IL)

(*) Notice: Subject to any disclaimer, the term of this patent is extended or adjusted under 35 U.S.C. 154(b) by 0 days.

(21) Appl. No.: 10/466,713

(22) PCT Filed: Jan. 28, 2002

(86) PCT No.: PCT/EP02/00846

§ 371 (c)(1),
(2), (4) Date: Nov. 24, 2003

(87) PCT Pub. No.: WO02/062743

PCT Pub. Date: Aug. 15, 2002

(65) Prior Publication Data

US 2004/0073058 A1 Apr. 15, 2004

(30) Foreign Application Priority Data

Feb. 2, 2001 (IT) ..................................... MI2001A0203

(51) Int. Cl.⁷ .................... C07C 69/76; C07C 229/00

(52) U.S. Cl. .......................... 560/61; 560/62; 560/45
(58) Field of Search ................. 560/45, 61, 62

(56) References Cited

U.S. PATENT DOCUMENTS 4,739,101 A * 4/1988 Bourgogne et al. ........... 560/61

* cited by examiner

Primary Examiner—Cecilia J. Tsang
Assistant Examiner—Taylor Victor Oh
(74) Attorney, Agent, or Firm—Walter H. Schneider

(57) ABSTRACT

A process for the preparation of fibrates of formula I

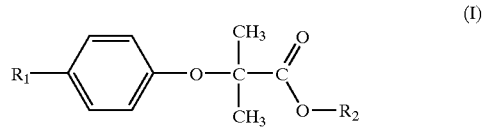

in which $R_1$ is a halogen atom, a 2,2-dichloro-cyclopropyl group, a (4-chlorophenyul)-hydroxymethyl group, a-4-chlorobenzoyl group or a 2-(4-chlorobenzamido)-ethyl group, and $R_2$ is hydrogen or a $C_1$–$C_4$ alkyl group.

3 Claims, No Drawings

PROCESS FOR THE PREPARATION OF FIBRATES

The present invention relates to a process for the preparation of fibrates of formula (I)

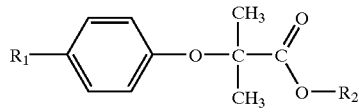

wherein $R_1$ is a halogen atom, a 2,2-dichloro-cyclopropyl group, a (4-chlorophenyl)-hydroxymethyl group, a 4-chlorobenzoyl group or a 2-(4-chlorobenzamido)-ethyl group, and $R_2$ is hydrogen or a $C_1$–$C_4$ alkyl group.

The compounds of formula (I) are known medicaments with hypocholesterolemic activity. In particular, fenofibrate, clofibrate and ciprofibrate have been widely used in clinic for some time in the treatment of dyslipidemias. The preparation thereof is disclosed, for example, in GB 860,303 (clofibrate), GB 1,415,295 (fenofibrate), GB 1,539,897.

According to an improved process for the preparation of the fibrates of formula (I), disclosed in EP-B-245,156 (Fournier, 11.11.1987), an alkyl 2-bromo-2-methyl-propionate of formula (II)

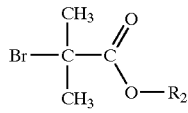

wherein $R_2$ is as defined above,
is reacted with a substituted phenol of formula (III)

wherein $R_1$ is as defined above,
in the absence of solvent and in the presence of a potassium carbonate excess, at temperatures above 120° C. for times longer than 2 hours.

It has now been found, and this is the object of the present invention, that the fibrates of formula (I) can advantageously be prepared by reacting the same compounds of formulae (II) and (III), as defined above, in the presence of potassium bicarbonate and of a solvent selected from $C_1$–$C_4$ alcohols and ketones at temperatures ranging from room temperature to 100° C.

The process of the invention is particularly suitable for the preparation of fenofibrate (compound of formula I wherein $R_1$ is 4-chloro-benzoyl).

Isopropanol is preferably used as the reaction solvent.

Potassium bicarbonate can be used in amounts sufficient to neutralize the halo acid formed during the reaction. The compound of formula (II) is preferably used in a stoichiometric excess to the compound of formula (III).

The solvent and the unreacted compound of formula (II) are evaporated off the reaction mixture and the residue is crystallized from a suitable solvent.

Compared with the method described in EP 245,156, the process of the present invention allows therefore to recover the reaction product directly from the reaction medium, without preventive purification of the crude product. Furthermore, there is no need for an acid excess to neutralize the potassium salt. As a consequence, the process of the invention is cost-saving and industrially advantageous compared with those of the prior art, in particular that disclosed in EP 245,156.

The following example illustrates the process of the invention in greater detail.

EXAMPLE

Isopropanol (400 ml), 4-chloro-4'-hydroxy-benzophenone (100 g, 0.431 mols), potassium bicarbonate (78 g, 0.78 mols), isopropyl α-bromo-isobutyrate (180 g, 0.865 mols) are loaded into a 2 l round-bottom flask at room temperature.

The solvent is refluxed (82–84° C. inner temperature) for 36 hours. After completion of the reaction, the solvent and the isopropyl α-bromo-isobutyrate excess are evaporated off under vacuum. The residue is taken up into acetone (400 ml) and insolubles are filtered off at room temperature. The filtered solution is concentrated to a residue and diluted with isopropyl alcohol (400 ml), then cooled at a temperature of 0–5° C. and the product is left to crystallize for at least 8 hours.

About 130 g of a product which meets the pharmacopoeia requirements are obtained (86% yield).

What is claimed is:

1. A process for the preparation of fibrates of formula (I)

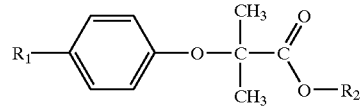

wherein $R_1$ as a halogen atom, a 2,2-dicloro-cyclopropyl group, a (4-chlorophenyl)-hydroxyethyl group, a 4-chlorobenzoyl group or a 2-(4-chlorobenzyamido)-ethyl group, and $R_2$ is hydrogen or a $C_1$–$C_4$ group, which process comprises reacting an alkyl 2-bromo-2-methyl-propionate of formula (II)

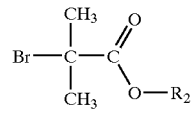

wherein $R_2$ is a defined above,
with a substituted phenol of formula (III)

wherein $R_1$ is defined as above;
said reaction being conducted in the presence of potassium bi-carbonate and a solvent selected from $C_1$–$C_4$ alcohols and ketones at a temperature ranging from room temperature to 100° C.; and recovering the reaction product directly from the reaction mixture by solvent evaporation followed by crystallization.

2. A process as claimed in claim 1 for the preparation of fenfibrate.

3. A process as claimed in claim 1 wherein the reaction solvent is isopropanol.

* * * * *